United States Patent
Chuang et al.

(10) Patent No.: US 11,384,150 B2
(45) Date of Patent: Jul. 12, 2022

(54) ANTIBODY-DRUG CONJUGATES AND USES THEREOF

(71) Applicants: Development Center for Biotechnology, New Taipei (TW); Tunghai University, Taichung (TW)

(72) Inventors: Shih-Hsien Chuang, New Taipei (TW); Wei-Ting Chao, Taichung (TW); Wei-Ting Sun, New Taipei (TW); Hui-Jan Hsu, New Taipei (TW); Wun-Huei Lin, New Taipei (TW)

(73) Assignees: Development Center for Biotechnology, New Taipei (TW); Tunghai University, Taichung (TW)

( * ) Notice: Subject to any disclaimer, the term of this patent is extended or adjusted under 35 U.S.C. 154(b) by 75 days.

(21) Appl. No.: 16/467,655

(22) PCT Filed: Dec. 13, 2017

(86) PCT No.: PCT/US2017/066074
§ 371 (c)(1),
(2) Date: Jun. 7, 2019

(87) PCT Pub. No.: WO2018/112027
PCT Pub. Date: Jun. 21, 2018

(65) Prior Publication Data
US 2020/0190199 A1     Jun. 18, 2020

Related U.S. Application Data

(60) Provisional application No. 62/434,035, filed on Dec. 14, 2016.

(51) Int. Cl.
| | |
|---|---|
| *C07K 16/28* | (2006.01) |
| *A61K 47/68* | (2017.01) |
| *A61P 35/00* | (2006.01) |
| *C07K 16/30* | (2006.01) |
| *A61K 38/00* | (2006.01) |
| *A61K 45/06* | (2006.01) |
| *A61K 39/00* | (2006.01) |
| *A61K 39/395* | (2006.01) |

(52) U.S. Cl.
CPC ...... *C07K 16/2863* (2013.01); *A61K 47/6803* (2017.08); *A61K 47/6849* (2017.08); *A61K 47/6851* (2017.08); *A61P 35/00* (2018.01); *C07K 16/30* (2013.01); *A61K 38/00* (2013.01); *A61K 45/06* (2013.01); *A61K 2039/505* (2013.01)

(58) Field of Classification Search
CPC .............. C07K 16/2863; C07K 16/30; C07K 2317/24; A61K 47/6851; A61K 47/6803; A61K 47/6849; A61K 38/00; A61K 45/06; A61K 2039/505; A61K 39/3955; A61K 31/553; A61P 35/00
See application file for complete search history.

(56) References Cited

U.S. PATENT DOCUMENTS

2015/0337042 A1    11/2015   Reilly et al.

FOREIGN PATENT DOCUMENTS

| WO | WO-2015/000062 A1 | 1/2015 | |
| WO | WO 2015/177279 A1 * | 11/2015 | ............. C08G 83/00 |
| WO | WO-2016/115218 A1 | 7/2016 | |

OTHER PUBLICATIONS

Akinaga S, Gomi K, Morimoto M, Tamaoki T, Okabe M. Antitumor activity of UCN-01, a selective inhibitor of protein kinase C, in murine and human tumor models. Cancer Res. Sep. 15, 1991;51(18):4888-92. PMID: 1893379. (Year: 1991).*
Tsuchida E, Tsuchida M, Urano M. Synergistic cytotoxicity between a protein kinase C inhibitor, UCN-01, and monoclonal antibody to the epidermal growth factor receptor on MDA-468 cells. Cancer Biother Radiopharm. Apr. 1997;12(2):117-21. doi: 10.1089/cbr.1997.12.117. PMID: 10851455. (Year: 1997).*
Kannaiyan R, Mahadevan D. A comprehensive review of protein kinase inhibitors for cancer therapy. Expert Rev Anticancer Ther. 2018;18(12):1249-1270. doi:10.1080/14737140.2018.1527688 (Year: 2018).*
Hwang et al "Structure-Based Prediction of Ligand-Protein Interactions on a Genome-Wide Scale" PNAS vol. 114, pp. 13685-13690, 2017.
Kiflemariam et al "Tumor Vessel Up-Regulation of INSR Revealed by Single-Cell Expression Analysis of the Tyrosine Kinome and Phosphatome in Human Cancers" The American Journal of Pathology vol. 185, pp. 1600-1609, 2015.

* cited by examiner

*Primary Examiner* — Hong Sang
*Assistant Examiner* — Sung Min Yoon
(74) *Attorney, Agent, or Firm* — Cesari & McKenna, LLP

(57) ABSTRACT

An immunoconjugate, comprising an anti-EGFR antibody or a binding fragment thereof, and a kinase inhibitor.

10 Claims, 4 Drawing Sheets

ANTIBODY-DRUG CONJUGATES AND USES THEREOF

CROSS-REFERENCE TO RELATED APPLICATION

This application is the National Stage of International Application No. PCT/US2017/066074, filed Dec. 13, 2017, which claims priority to U.S. Provisional Application No. 62/434,035, filed on Dec. 14, 2016. The contents of both prior applications are hereby incorporated by reference herein in their entirety.

BACKGROUND

Targeted therapies (e.g., antibodies) have emerged as important players in the fight against cancer. However, it has been observed that many individuals are resistant to such therapies. Cetuximab, which is a chimeric mouse-human monoclonal antibody that specifically binds to epidermal growth factor receptor (EGFR), is approved for the treatment of colorectal cancer and head and neck cancer. Cetuximab is not effective against cancers that harbor certain mutations, such as mutations in KRAS, BRAF, PIK3CA, and PTEN. It has been shown that MET and SRC activation by cetuximab may be a mechanism for the drug resistance. See, Song et al., Int. J. Mol. Sci., 15:5838-5851 (2014).

Antibody-drug conjugates (ADCs) allow targeted delivery of cytotoxic agents to specific cancer cells. Thus, development for cancer therapies has been directed toward ADCs. On the other hand, there are concerns about the side effects of ADCs, as they carry potent cytotoxic agents. Clinical studies also suggest that ADCs may also be ineffective in certain individuals.

SUMMARY

In one aspect, provided herein is an immunoconjugate that contains an anti-EGFR antibody or a binding fragment thereof, and a kinase inhibitor.

In some embodiments, the kinase inhibitor is an SRC inhibitor. For example, it can be selected from the group consisting of 1-Naphthyl PP1, A 419259 trihydrochloride, AGL 2263, altenusin, ansatrienin A, AP 24534, AZM 475271, Bcr-abl inhibitor II, NVP-BHG712, bosutinib, calphostin C, damnacanthal, dasatinib, geldanamycin, staurosporine, herbimycin A, indirubin-3'-(2,3-dihydroxypropyl) shyoximether, KB SRC 4, KX2-391, lavendustin A, LCB 03-0110 dihydrochloride, luteolin, MNS, neratinib, PD 166285 dihydrochloride, PD 180970, JNJ-10198409, pelitinib, piceatannol, PKC-412, PKI 166 hydrochloride, PP1, PP2, quercetin, saracatinib, SKI-1, SU6656, TC-S 7003, TX-1123, P21d hydrochloride, Tilfrinib, vandetanib, sunitinib, imatinib, WH-4-023, tesevatinib, ENMD-2076, TPX-0005, AZD-0424, KX2-361, CCT196969, and TX-1918.

In some embodiments, the anti-EGFR antibody is selected from the group consisting of cetuximab, panitumumab, necitumumab, zalutumumab, matuzumab, nimotuzumab, trastuzumab, ior-egf/r3, futuximab, depatuxizumab, duligotuzumab, or tomuzotuximab.

Any of the immunoconjugates described herein can have the formula Ab-(L-D)m, Ab being the anti-EGFR antibody or a binding fragment thereof, L being a linker, D being the kinase inhibitor, and m being a number from 1-20 (e.g., 1, 2, 3, 4, 5, 6, 7, 8, 9, 10, 11, 12, 13, 14, 15, 16, 17, 18, 19, 20, 1-10, 1-15, 5-15, 5-20, 2-15, or 2-8).

In some embodiments, the immunoconjugate has the following formula:

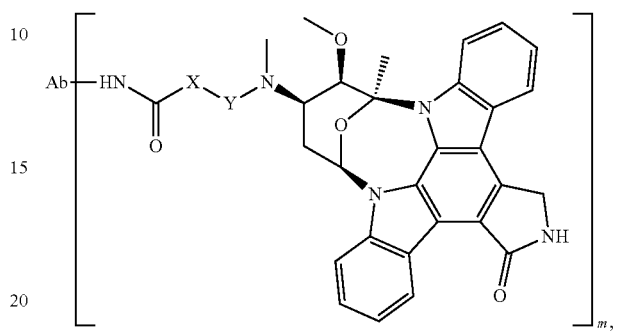

in which

X is —(CH$_2$)$_n$—,

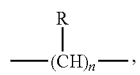

or —Ar—; R is hydrogen or an alkyl; Ar is

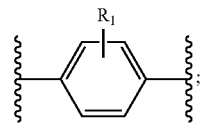

R$_1$ is hydrogen, halogen, or an alkyl; n is an integer of 1-10; Y is

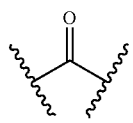 [SMILES: *C(*)=O]

or —CH$_2$—; and m is an integer of 1-20. For example, the immunoconjugate can be

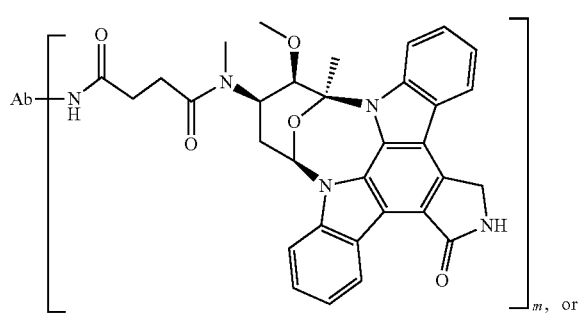

or

-continued
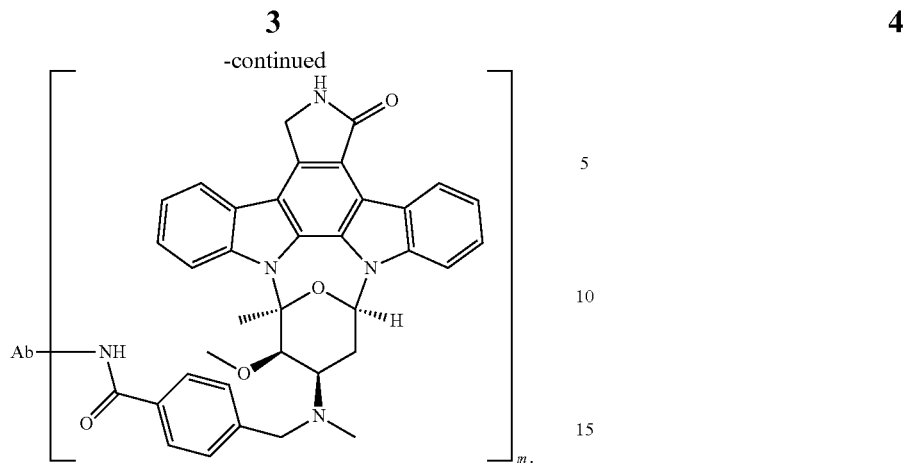
In some embodiments, the immunoconjugate has the following formula:
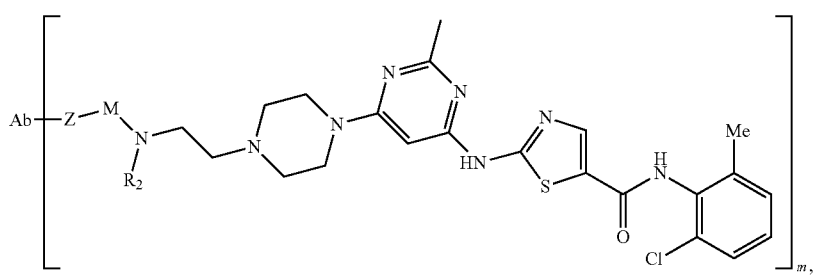
in which
Z is NH or S; M is
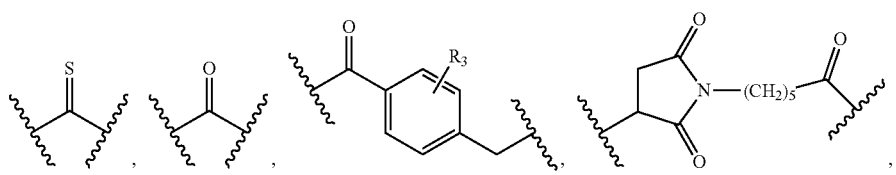
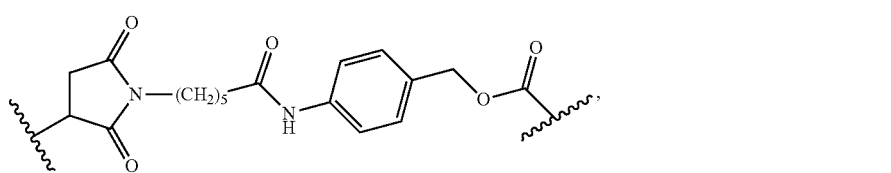
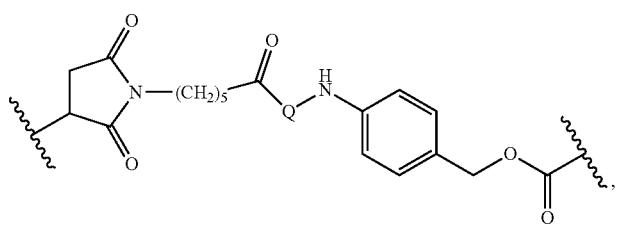

-continued
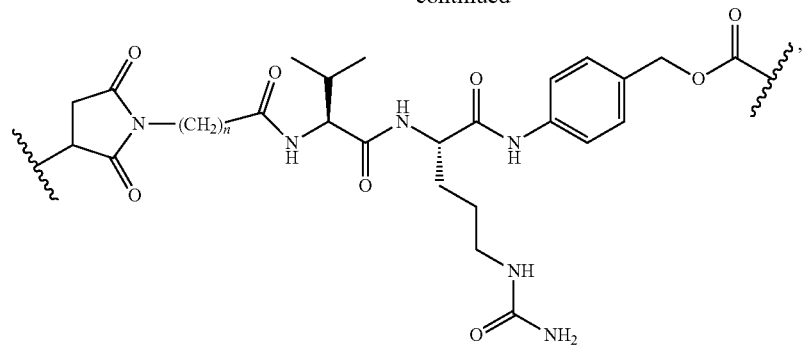
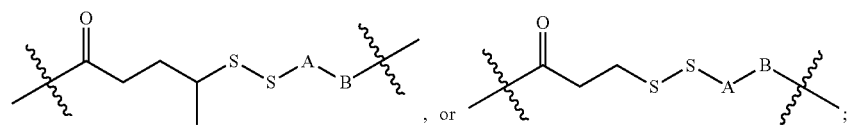
$R_2$ is hydrogen or
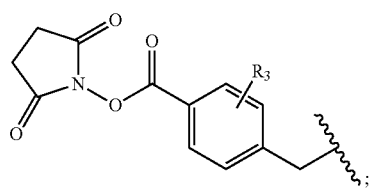
m is an integer of 1-20; Q is -peptide-, -L-phenylalanine-L-lysine-, or -L-valine-L-citrulline-; $R_3$ is hydrogen, halogen, or an alkyl; A is $-CH_2)_n-$,
$$-(CH)_n- \overset{R}{|}$$,
or $-Ar-$; B is $-(CH_2)_n-$ or
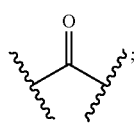 [SMILES: *C(*)=O]
R is hydrogen or an alkyl; Ar is
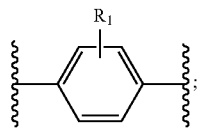
$R_1$ is hydrogen, halogen, or an alkyl; and n is an integer of 1-10. In some embodiments, the immunoconjugate is
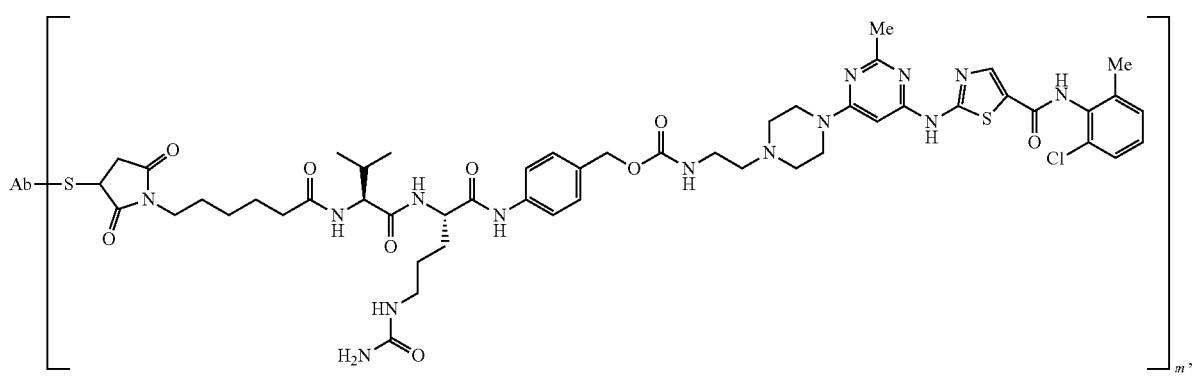

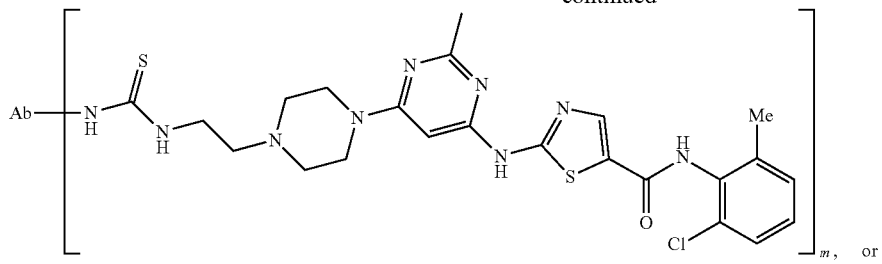

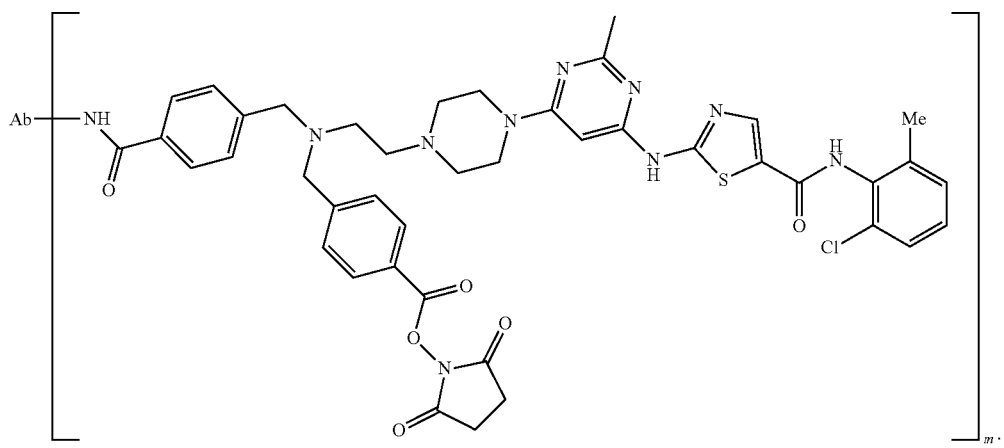

In another aspect, provided herein is a pharmaceutical composition that contains any of the immunoconjugates described herein and a pharmaceutically acceptable carrier. The pharmaceutical composition can contain another therapeutic agent.

In yet another aspect, provided herein is a method of inhibiting a cancer cell that includes contacting the cancer cell with an effective amount of any of the immunoconjugates described herein.

In one aspect, a method of treating a cancer in a subject is provided herein. It includes administering an effective amount of any of the immunoconjugates described herein to the subject.

In some embodiments, the cancer in the subject is resistant to an anti-EGFR antibody or a binding fragment thereof, or an EGFR tyrosine kinase inhibitor. In some embodiments, the cancer has a mutation in KRAS, BRAF, PIK3CA, PTEN, EGFR, P53, or SRC. Prior to the administering step, the method can include determining whether the cancer has the mutation. Optionally, the method can further administering another therapeutic agent to the subject.

In some embodiments, the cancer is a colorectal cancer, head and neck cancer, gastrointestinal cancer, lung cancer, breast cancer, pancreatic cancer, ovarian cancer, cervical cancer, prostate cancer, kidney cancer, brain cancer, renal carcinoma, glioma, bladder cancer, oral cancer, or EGFR-positive cancer.

In another aspect, described herein is a staurosporine derivative, wherein the derivative is

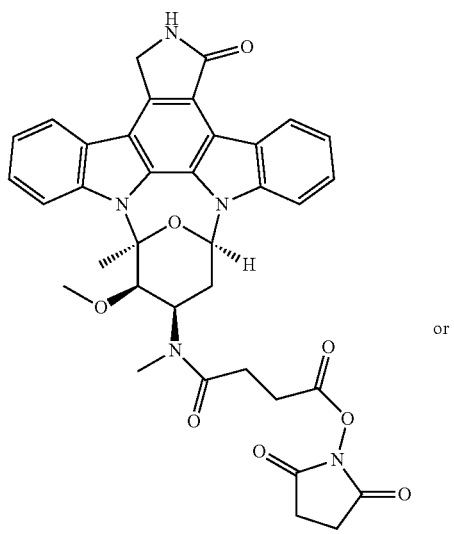

or

-continued

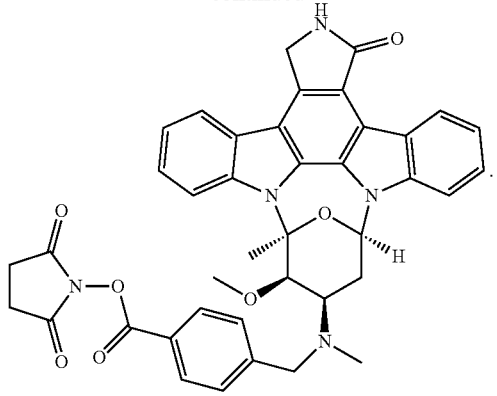

In yet another aspect, provided herein is a dasatinib derivative, wherein the derivative is In one aspect, provided herein is a method of preparing an immunoconjugate. The method includes coupling an antibody or a binding fragment thereof to the staurosporine derivative or dasatinib derivative described herein. In one embodiment, the antibody is cetuximab.

The details of one or more embodiments are set forth in the accompanying drawing and the description below. Other features, objects, and advantages of the embodiments will be apparent from the description and drawing, and from the claims.

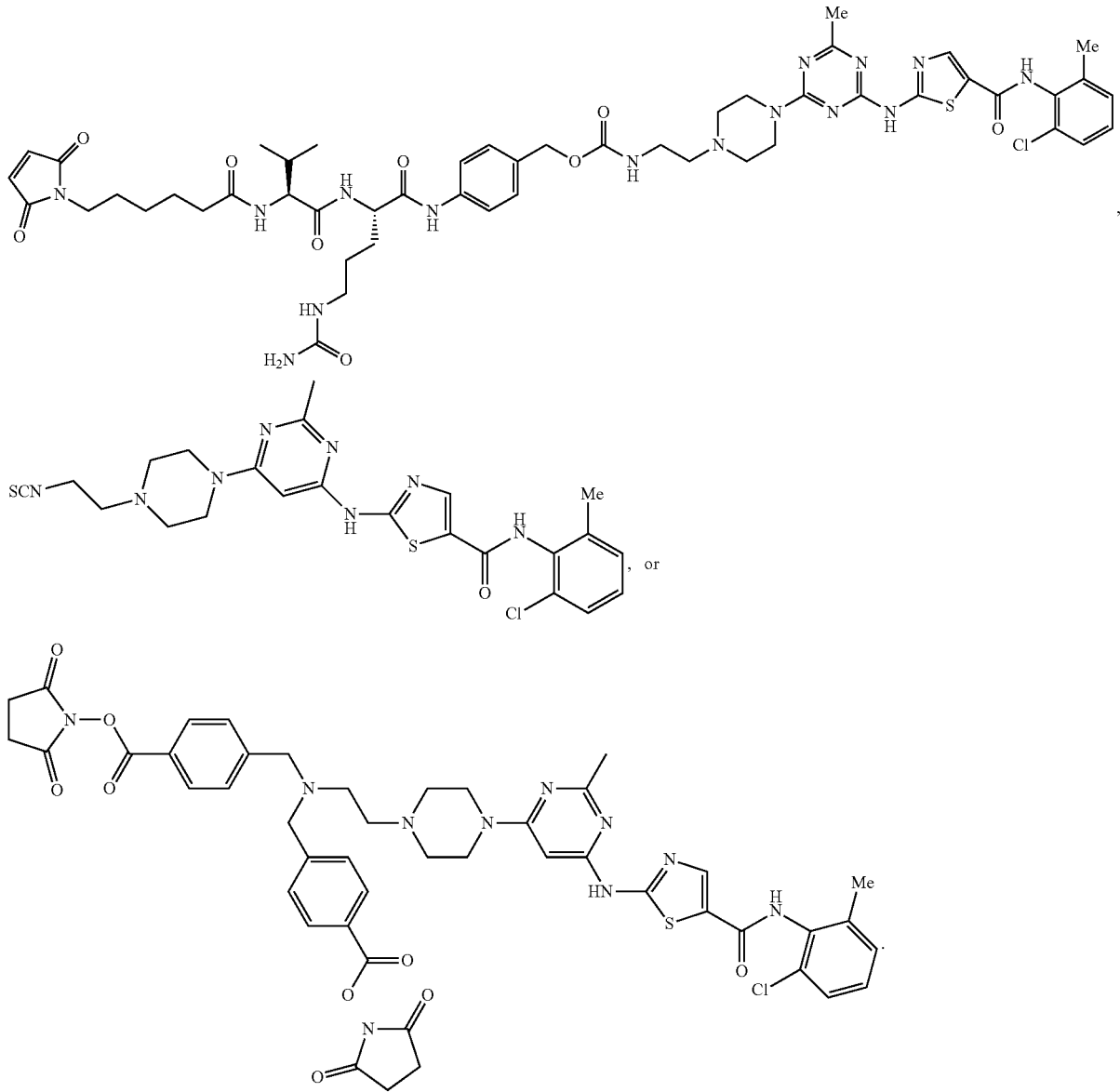

Figure 2:
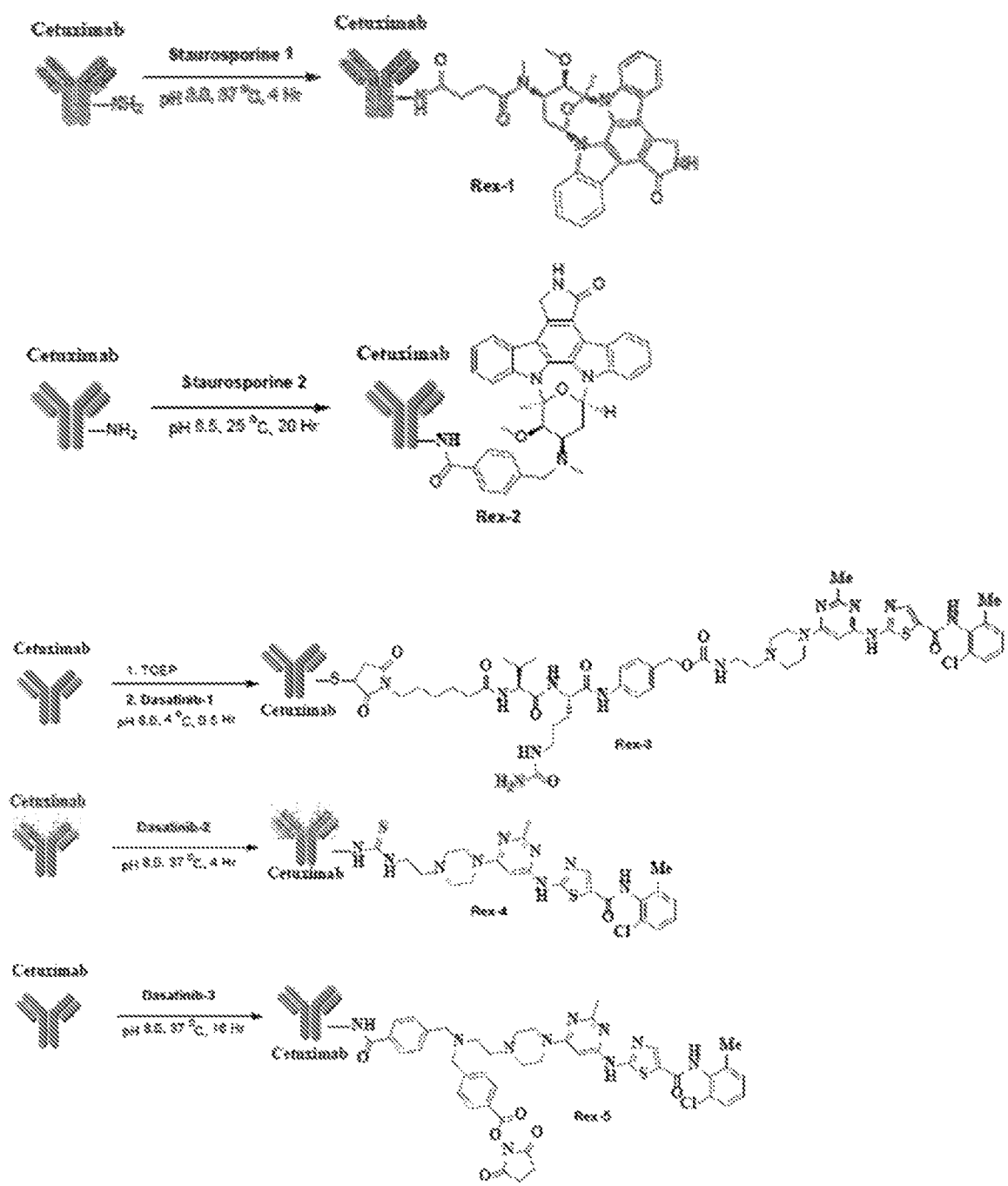

FIG. 2 shows exemplary antibody-drug conjugates.

Figure 3:
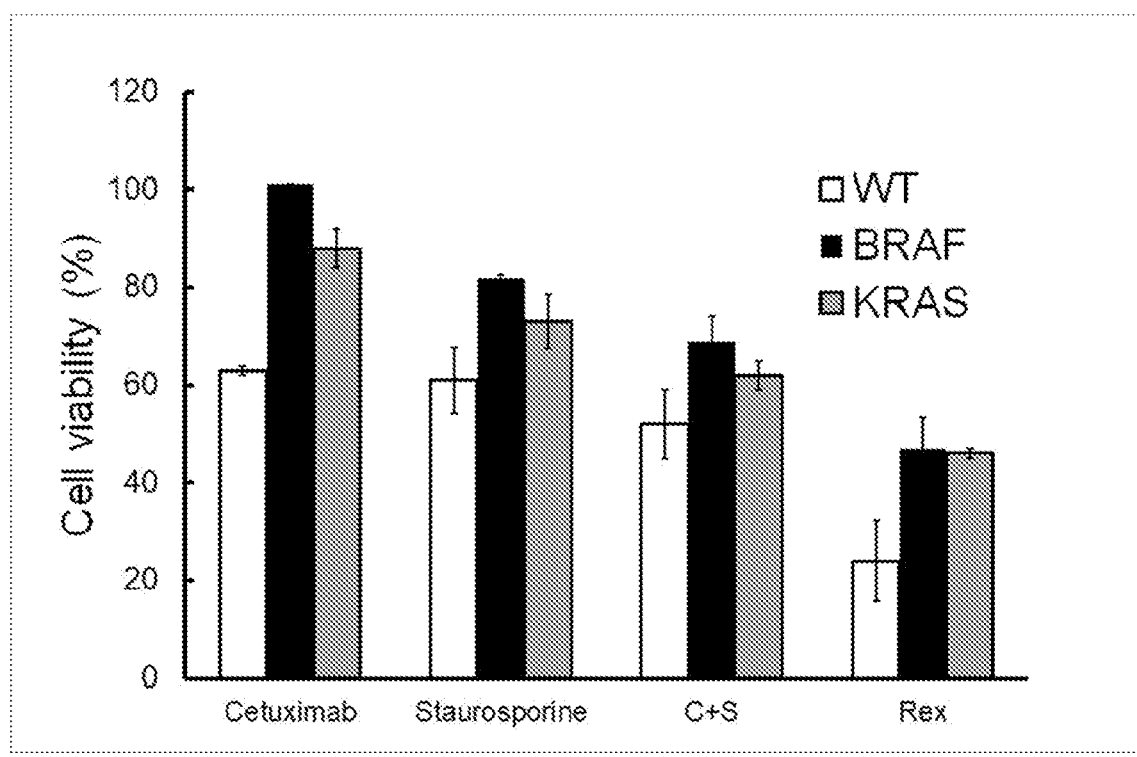

FIG. 3 shows efficacy of cetuximab (1 ug/ml), staurosporine (10 nM), cetuximab (C) and staurosporine (S) combined, and Rex-1 (1 ug/ml) on SW48 (WT), HT-29 (BRAF), and SW480 (KRAS) colon cancer cell lines.

Figure 4:
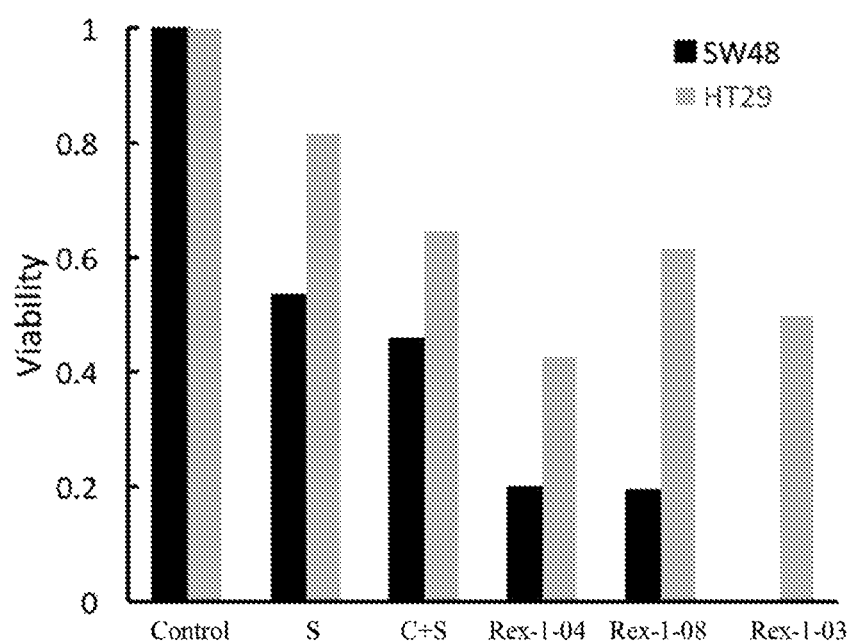

FIG. 4 shows efficacy of different lots of Rex-1 on SW48 and HT-29 (BRAF) cells lines. C: cetuximab; S: staurosporine.

DETAILED DESCRIPTION

It was unexpectedly discovered that an immunoconjugate containing an anti-EGFR antibody and a kinase inhibitor, e.g., a SRC inhibitor, was more effective for treating cancers harboring certain mutations than the antibody alone or in combination with the kinase inhibitor. Accordingly, provided herein is an immunoconjugate that includes an anti-EGFR antibody and a kinase inhibitor.

The kinase inhibitor can be one that inhibits a kinase selected from the group consisting of AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MSTIR, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, ZAP70, MAPK, ERK, PI3K, AKT, FAK, PKC, and PKA.

In some embodiments, the kinase inhibitor is an SRC inhibitor. SRC inhibitors include, but are not limited to, 1-Naphthyl PP1, A 419259 trihydrochloride, AGL 2263, altenusin, ansatrienin A, AP 24534, AZM 475271, Bcr-abl inhibitor II, NVP-BHG712, bosutinib, calphostin C, damnacanthal, dasatinib, geldanamycin, staurosporine, herbimycin A, indirubin-3'-(2,3-dihydroxypropyl)shyoximether, KB SRC 4, KX2-391, lavendustin A, LCB 03-0110 dihydrochloride, luteolin, MNS, neratinib, PD 166285 dihydrochloride, PD 180970, JNJ-10198409, pelitinib, piceatannol, PKC-412, PKI 166 hydrochloride, PP1, PP2, quercetin, saracatinib, SKI-1, SU6656, TC-S 7003, TX-1123, P21d hydrochloride, Tilfrinib, vandetanib, sunitinib, imatinib, WH-4-023, tesevatinib, ENMD-2076, TPX-0005, AZD-0424, KX2-361, CCT196969, and TX-1918. For example, the SRC inhibitor can be staurosporine or dasatinib.

The term "antibody" as used herein includes various antibody structures that have an antigen-binding activity, including but not limited to monoclonal antibodies, polyclonal antibodies, full-length antibodies or fragments thereof, antibodies that contain an Fc region, Fab fragments, Fab' fragments, F(ab')$_2$ fragments, single-chain antibodies, scFV multimers, monovalent antibodies, multivalent antibodies, humanized antibodies and chimeric antibodies.

Various anti-EGFR antibodies are known in the art or commercially available. Such antibodies can also be generated using methods known in the art, e.g., recombinant methods. In some embodiments, the antibody is selected from the group consisting of cetuximab, panitumumab, necitumumab, zalutumumab, matuzumab, nimotuzumab, trastuzumab, ior-egf/r3, futuximab, depatuxizumab, duligotuzumab, and tomuzotuximab.

The immunoconjugate described herein can have the formula Ab-(L-D)m, in which Ab is an anti-EGFR antibody, L is a linker, D is a kinase inhibitor, and m is a number (e.g., an integer) from 1 to 20.

The linker can be a cleavable or non-cleavable linker. Exemplary linkers include, but are not limited to, maleimidocaproyl linker, maleimidocaproyl-p-aminobenzylcarbamate, maleimidocaproyl-peptide-aminobenzylcarbamate, maleimidocaproyl-L-phenylalanine-L-lysine-p-aminobenzylcarbamate, maleimidocaproyl-L-valine-L-citrulline-p-aminobenzylcarbamate, N-succinimidyl 3-(2-pyridyldithio)propionate, 4-succinimidyl-oxycarbonyl-2-methyl-2-(2-pyridyldithio)-toluene, N-succinimidyl 3-(2-pyridyldithio)propionate, N-succinimidyl 4-(2-pyridyldithio)butyrate, 2-iminothiolane, S-acetylsuccinic anhydride, disulfide benzyl carbamate, carbonate, hydrazone, N-(a-maleimidoacetoxy) succinimide ester, N-[4-(p-azidosalicylamido) butyl]-3'-(2'-pyridyldithio)propionamide, N-[b-maleimidopropyloxy]succinimide ester, [N-e-maleimidocaproyloxy]succinimide ester, N-[g-maleimidobutyryloxy]succinimide ester, succinimidyl-4-[N-maleimidomethyl]cyclohexane-1-carboxy-[6-amidocaproate], succinimidyl 6-(3-[2-pyridyldithiol-propionamido)hexanoate, m-maleimidobenzoyl-N-hydroxysuccinimide ester, N-succinimidyl[4-iodoacetyl]aminobenzoate, succinimidyl 44N-maleimidomethyl]cyclohexane-1-carboxylate, N-succinimidyl 3-[2-pyridyldithio]-propionamido, [N-e-maleimidocaproyloxy]sulfosuccinimide ester, N-[g-maleimidobutyryloxy]sulfosuccinimide ester, sulfosuccinimidyl-6-methyl-α-(2-pyridyldithio)toluamido]hexanoate), sulfosuccinimidyl 6-(3'-[2-pyridyldithio]-propionamido)hexanoate, m-maleimidobenzoyl-N-hydroxysulfosuccinimide ester, N-sulfosuccinimidyl[4-iodoacetyl]aminobenzoate, sulfosuccinimidyl 4-[N-maleimidomethyl] cyclohexane-1-carboxylate, sulfosuccinimidyl 4-[p-maleimidophenyl]butyrate, ethylene glycol-bis(succinic acid N-hydroxysuccinimide ester), disuccinimidyl tartrate, 1,4,7,10-tetraazacyclododecane-1,4,7,10-tetraacetic acid, diethylenetriamine-pentaacetic acid, and thiourea linker.

In some embodiments, the immunoconjugate contains staurosporine and has the following formula:

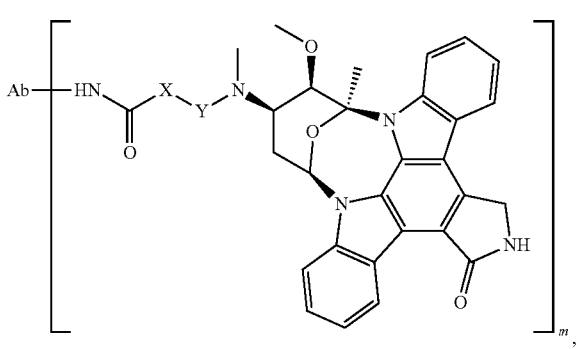

in which
X is —(CH$_2$)$_n$—,

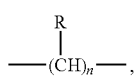

or —Ar—; R is hydrogen or an alkyl; Ar is
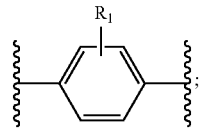
$R_1$ is hydrogen, halogen, or an alkyl; n is an integer of 1-10; Y is
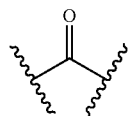 [SMILES: *C(*)=O]
or —CH$_2$—; and m is an integer of 1-20 (e.g., 1, 2, 3, 4, 5, 6, 7, 8, 9, 10, 11, 12, 13, 14, 15, 16, 17, 18, 19, 20, 1-10, 1-15, 5-15, 5-20, 2-15, or 2-8). Two exemplary conjugates are:
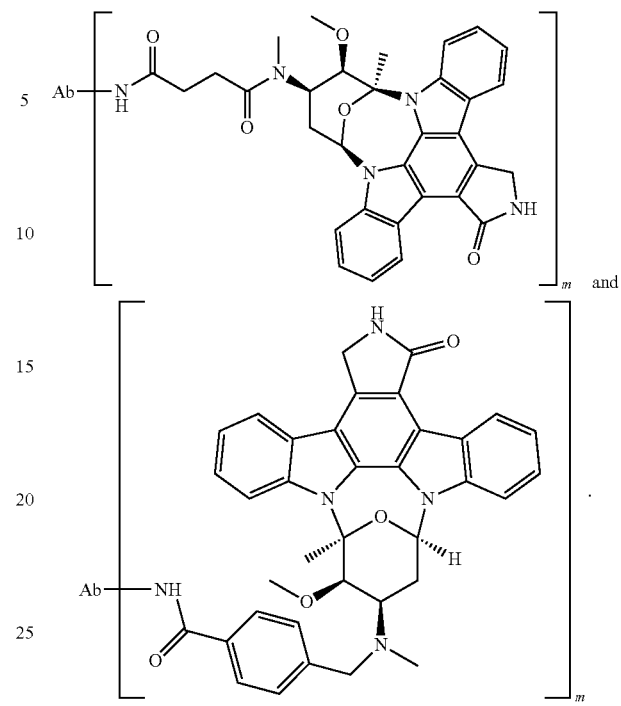
In some embodiments, the immunoconjugate contains dasatinib and has the following formula:
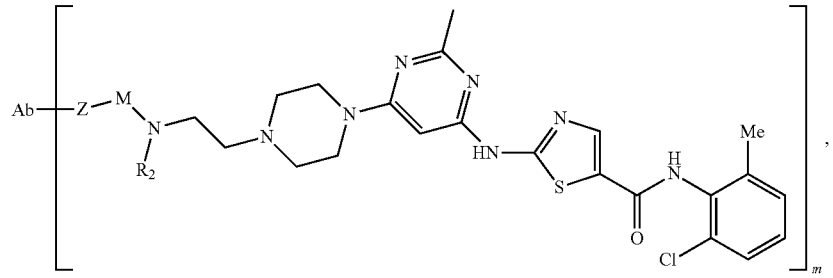
in which
Z is NH or S;
M is
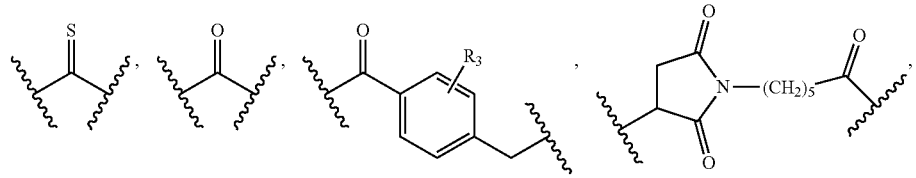
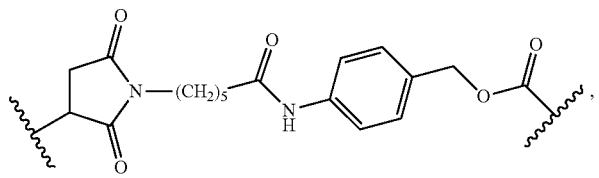

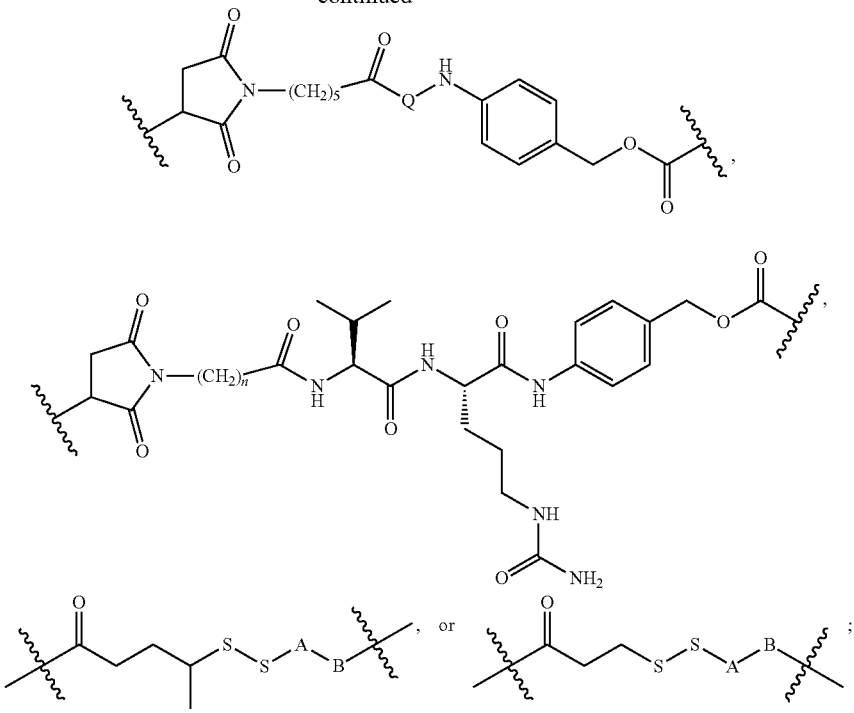

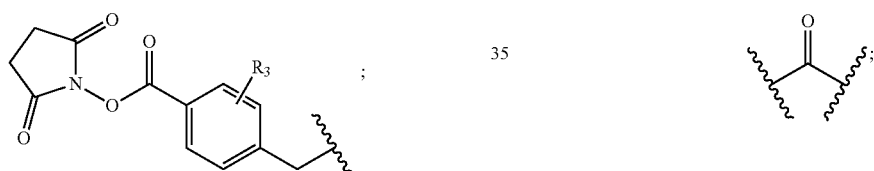

R$_2$ is hydrogen or

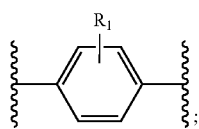

m is an integer of 1-20; Q is -peptide-, -L-phenylalanine-L-lysine-, or -L-valine-L-citrulline-; R$_3$ is hydrogen, halogen, or an alkyl; A is —(CH$_2$)$_n$—, —(CH)$_n$— with R substituent, or —Ar—; B is —(CH$_2$)$_n$— or (carbonyl group);

R is hydrogen or an alkyl; Ar is (para-substituted phenyl with R$_1$);

R$_1$ is hydrogen, halogen, or an alkyl; and n is an integer of 1-10. Three exemplary immunoconjugates are:

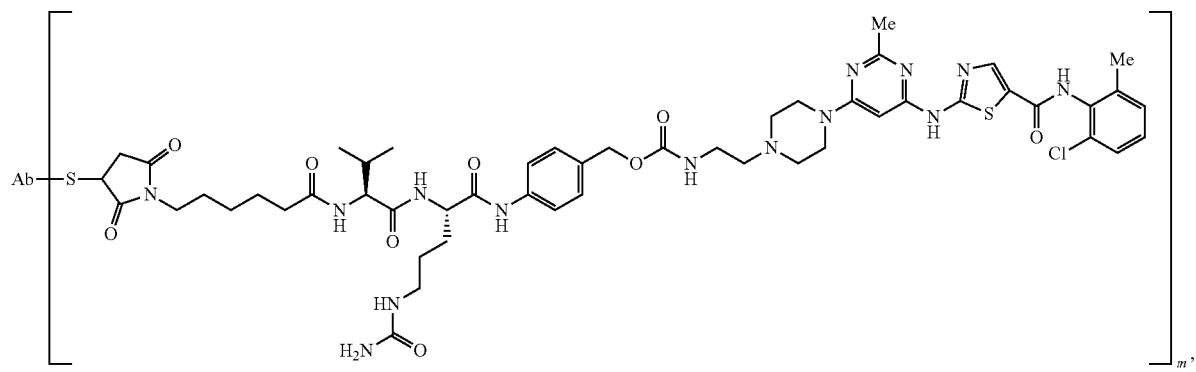

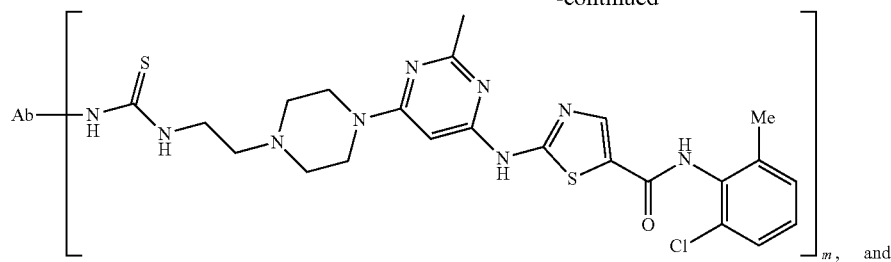

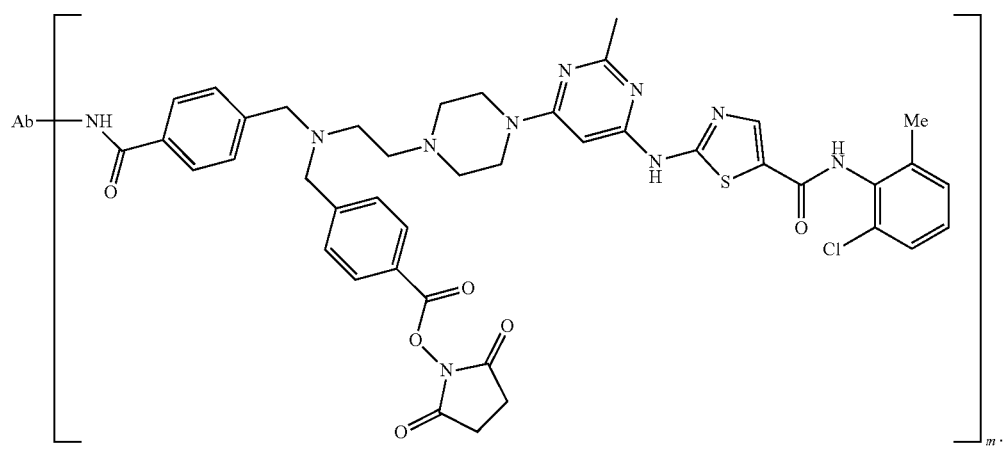

Methods of conjugating a compound to an antibody via a linker are known in the art, including methods described in the examples below. A derivative of the compound containing a linker can be generated first and then conjugated to an antibody.

For example, shown below are two staurosporine linker derivatives that can each be conjugated to an anti-EGFR antibody (e.g., cetuximab) to prepare an immunoconjugate.

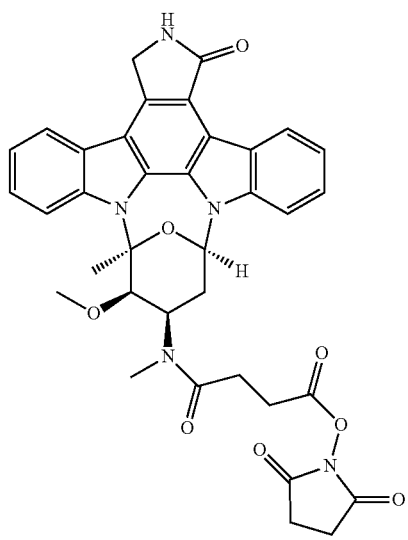

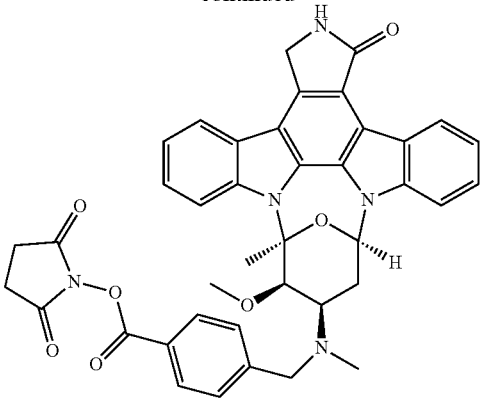

Three exemplary dasatinib linker derivatives are shown below. Each of them can be conjugated to an anti-EGFR antibody (e.g., cetuximab) to prepare an immunoconjugate.

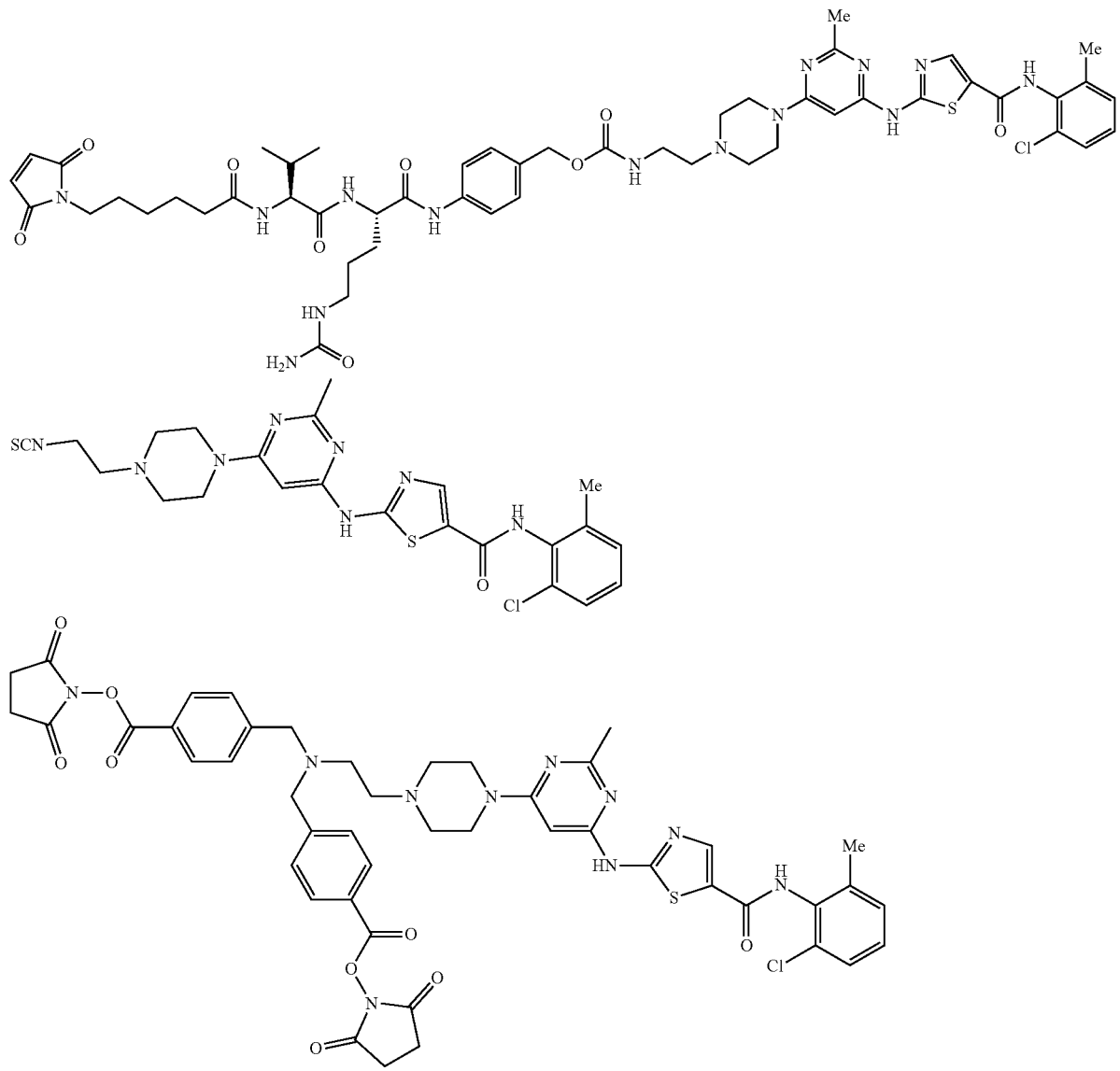

The immunoconjugate described herein can be used to treat a cancer or tumor in a subject, e.g., an EGFR-positive cancer or tumor. The cancer or tumor can be a colorectal cancer, head and neck cancer, gastrointestinal cancer, lung cancer, breast cancer, pancreatic cancer, ovarian cancer, cervical cancer, prostate cancer, kidney cancer, brain cancer, renal carcinoma, glioma, bladder cancer, or oral cancer. Optionally, before a subject is treated with the immunoconjugate, it can be determined whether the cancer or tumor in the subject expresses EGFR using methods known in the art.

In some embodiments, the cancer or tumor is resistant to an EGFR-targeted therapy, e.g., an anti-EGFR antibody or EGFR tyrosine kinase inhibitor. The mechanism of the drug resistance may or may not be known. In some embodiments, the cancer or tumor has a mutation that is associated or correlated with resistance to an EGFR-targeted therapy, e.g., a mutation in KRAS, BRAF, PIK3CA, PTEN, EGFR, P53, or SRC. Optionally, before a subject is treated with the immunoconjugate, it can be determined whether the cancer or tumor in the subject exhibits resistant to an EGFR-targeted therapy or carries a mutation associated with drug resistance. A subject who has previously shown resistance to an EGFR-targeted therapy may also be a candidate to be treated with the immunoconjugate described herein.

Any of the immunoconjugates described herein can be formulated as a pharmaceutical composition suitable for various routes of administration, e.g., intravenous, intraarticular, conjunctival, intracranial, intraperitoneal, intrapleural, intramuscular, intrathecal, or subcutaneous route of administration. The pharmaceutical composition can be an aqueous solution or lyophilized formulation. It can contain a pharmaceutically acceptable carrier, e.g., a buffer, excipient, stabilizer, or preservative. The pharmaceutical composition can include other active ingredients that work together with the immunoconjugate, e.g., another therapeutic agent. The pharmaceutical composition can be used to treat a cancer or tumor in a subject.

A "subject" refers to a human or a non-human animal. "Treating" or "treatment" refers to administration of a compound or composition to a subject, who has a disorder, with the purpose to cure, alleviate, relieve, remedy, delay the onset of, or ameliorate the disorder, the symptom of the disorder, the disease state secondary to the disorder, or the predisposition toward the disorder. An "effective amount" refers to an amount of the compound or composition that is capable of producing a medically desirable result in a treated subject.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

Example 1: Inhibition of Cetuximab-Induced SRC Activation

Figure 1:
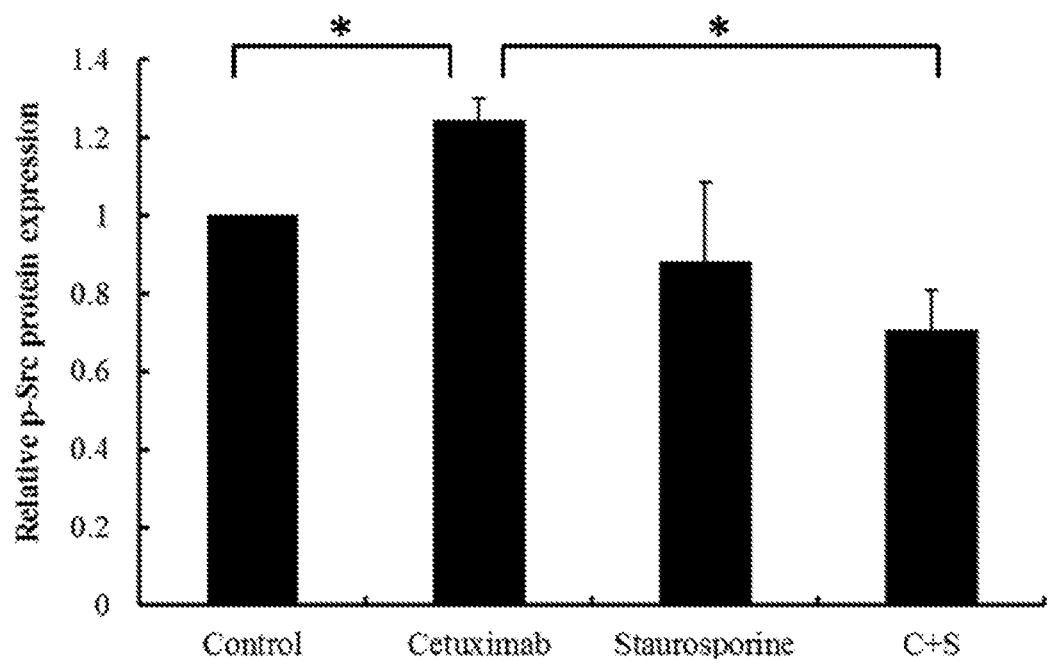
FIG. 1 shows that staurosporine and cetuximab combined inhibited Src activation in SW480 colon cells. C: cetuximab; S: staurosporine; p-Src: phosphorylated Src (activated). *significant difference (p<0.05). Quantification values were from western blot analysis of protein expression.

A colon cancer cell line with a mutation in KRAS, i.e., SW480, was analyzed to determine whether the combination of an Src inhibitor and cetuximab could inhibit SRC activation. As shown in FIG. 1, cells treated with the combination exhibited significantly reduced level of Src protein as compared to cells treated with either staurosporine or cetuximab.

Example 2: Design and Synthesis of Staurosporine Linker Derivatives

Scheme 1 below shows synthesis of staurosporine 1 linker derivative. Staurosporine could react with succinic anhydride by the secondary amine. Staurosporine carboxylic acid 1 was converted to an N-Hydroxysuccinimide (NHS) group via N-hydroxysuccinimide (HOSu) and 1-ethyl-3-(3-dimethylaminopropyl)carbodiimide (EDCI) treatment. Staurosporine 1 can then be conjugated with an antibody via the NHS group.

Scheme 1

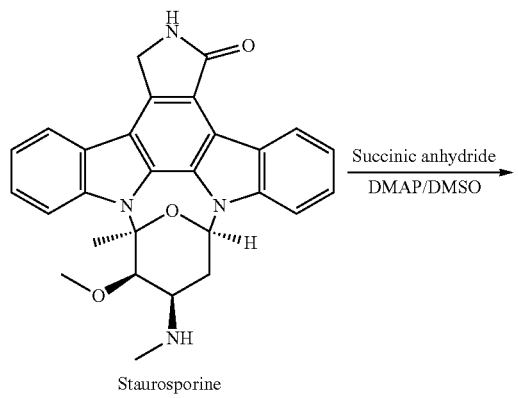

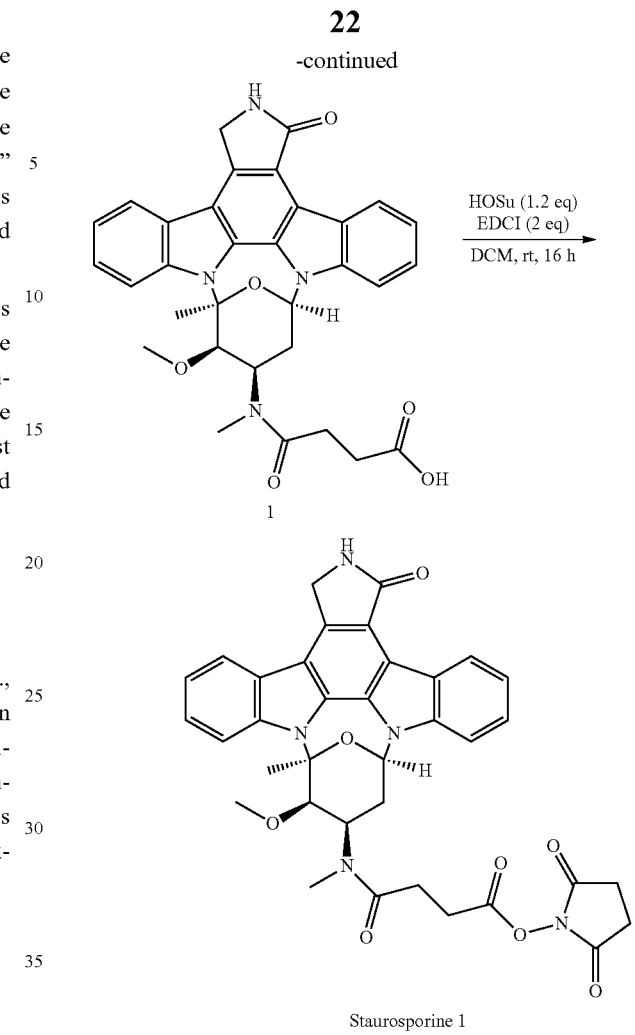

Staurosporine 1

Referring to scheme 1, to a solution of staurosporine (10 μmol) in dimethyl sulfoxide (DMSO), succinic anhydride (15 μmol) and 4-dimethylaminopyridine (DMAP) (20 μmol) were added in the dark. After 30 h of stirring, the mixture was precipitated with 0.1% trifluoroacetic acid (TFA) in water, and the precipitate was triturated twice with 0.1% TFA in water to afford compound 1 in 84 yield. $^1$H NMR (300 MHz, DMSO-$d_6$) δ 12.06 (s, 1H), 9.29 (d, J=7.9 Hz, 1H), 8.59 (s, 1H), 8.05 (d, J=7.7 Hz, 1H), 7.99 (d, J=8.5 Hz, 1H), 7.67 (d, J=8.2 Hz, 1H), 7.48 (t, J=7.7 Hz, 2H), 7.35 (t, J=7.5 Hz, 1H), 7.29 (t, J=7.5 Hz, 1H), 7.03 (t, J=7.5 Hz, 1H), 5.00 (s, 3H), 4.22 (s, 1H), 2.81 (s, 3H), 2.77 (s, 3H), 2.68 (d, J=5.6 Hz, 1H), 2.60-2.56 (m, 2H), 2.33 (s, 3H), 2.28-2.17 (m, 1H). LCMS m/z calcd for C32H30N4O6 [M+H]$^+$= 567.220, found 567.199 (IT-TOF).

To a solution of staurosporine-CO$_2$H (1, 160 mg, 0.282 mmol) in tetrahydrofuran (THF) (3 ml), HOSu (39 mg, 0.338 mmol) and 1-ethyl-3-(3-dimethylaminopropyl)carbodiimide (EDCI) (88 mg, 0.564 mmol) were added. The reaction mixture was stirred at room temperature for 16 hours and then quenched with water. The solution was extracted with CH$_2$Cl$_2$. The organic layer was washed with brine, dried over MgSO$_{4(s)}$, and concentrated under reduced pressure to yield staurosporine 1 (153 mg) as a pale white solid in 82% yield. $^1$H NMR (600 MHz, DMSO-d$_6$); $^1$H NMR (600 MHz, DMSO-d$_6$) δ 9.3-9.3 (m, 1H), 8.6 (d, J=5.2 Hz, 1H), 8.1 (t, J=8.2 Hz, 1H), 8.0 (dd, J=11.2, 8.5 Hz, 1H), 7.7 (dd, J=8.2, 5.2 Hz, 1H), 7.5-7.5 (m, 2H), 7.4 (q, J=7.7 Hz, 1H), 7.3 (ddd, J=8.0, 7.0, 1 Hz, 1H), 7.0 (ddd, J=8.5, 6.7, 3.6 Hz, 1H), 5.0-5.0 (m, 3H), 4.2 (ddd, J=12.0, 2.8, 1.5 Hz, 1H), 3.0 (t, J=6.3 Hz, 1H), 2.9-2.8 (m, 5H), 2.8 (s, 1H), 2.8 (s, 2H), 2.7-2.7 (m, 1H), 2.7-2.6 (m, 1H), 2.6 (s, 2H), 2.5-2.5 (m, 1H), 2.3 (d, J=8.5 Hz, 2H), 2.2 (tdd, J=12.0, 8.2, 6.7 Hz, 1H); $^{13}$C NMR (600 MHz, DMSO-d$_6$) 173.3, 172.4, 171.2, 170.7, 169.2, 139.3, 136.7, 133.1, 129.6, 129.6, 126.1, 125.8, 125.5, 124.2, 123.1, 121.9, 120.8, 119.9, 119.9, 115.7, 114.6, 114.1, 109.5, 95.1, 83.6, 82.7, 60.9, 48.8, 45.9, 31.2, 29.9, 28.3, 27.2, 26.6, 25.9, 25.7; ESI-MS m/z 664.67 ([M+1]$^+$).

Scheme 2 below shows synthesis of staurosporine 2 linker derivatives. Staurosporine was reacted with N-succinimidyl-4-formylbenzamide and sodium cyanoborohydride to convert the amino group to an NHS group. Staurosporine 2 can then be conjugated with an antibody via the NHS group.

Scheme 2

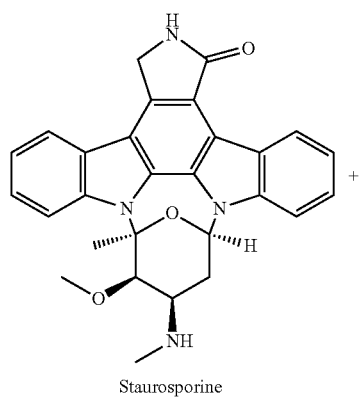

Staurosporine

+

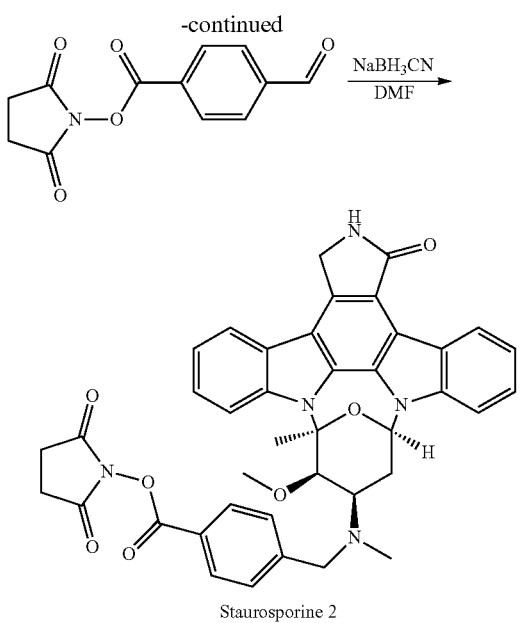

Staurosporine 2

Referring to scheme 2, N-succinimidyl-4-formylbenzamide (127 mg, 0.51 mmol), sodium cyanoborohydride (24 mg, 0.38 mmol), and acetic acid (0.196 mL) were added to a solution of staurosporine (80 mg, 0.17 mmol) in dimethylformamide (DMF) (5 ml). The reaction mixture was stirred at room temperature for 16 hours. DMF and acetic acid were removed by rotary evaporator. The residue was extracted with DCM. The organic layer was washed with brine, dried over MgSO$_{4(s)}$, and concentrated under reduced pressure. Staurosporine 2 was purified by column chromatography (DCM:MeOH=9:1) to give a white solid in 35% yield.

Example 3: Design and Synthesis of Dasatinib Linker Derivatives

Scheme 3 below shows the synthesis of dasatinib-1 with a cleavable valine-citrulline linker. The hydroxyl group of dasatinib was converted to an amine group by Mitsunobu reaction and hydrazine deprotaction. See CN106279143. The leaving group p-nitrophenol of Mal-C5-VC-PAB-PNP was substituted by the amine of dasatinib-NH$_2$. The product dasatinib-1 can then be conjugated with an antibody through thioether bond formation.

Scheme 3

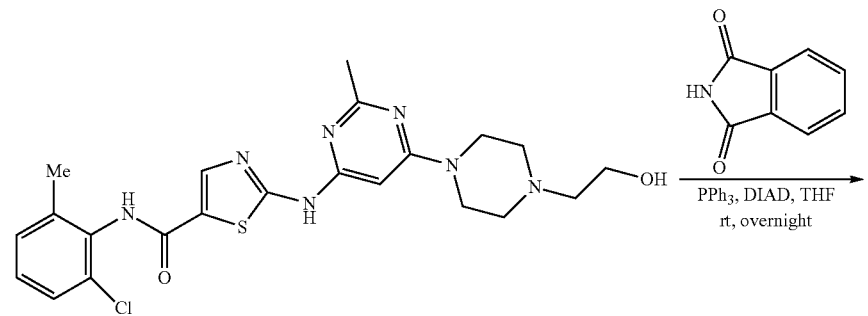

dasatinib

-continued
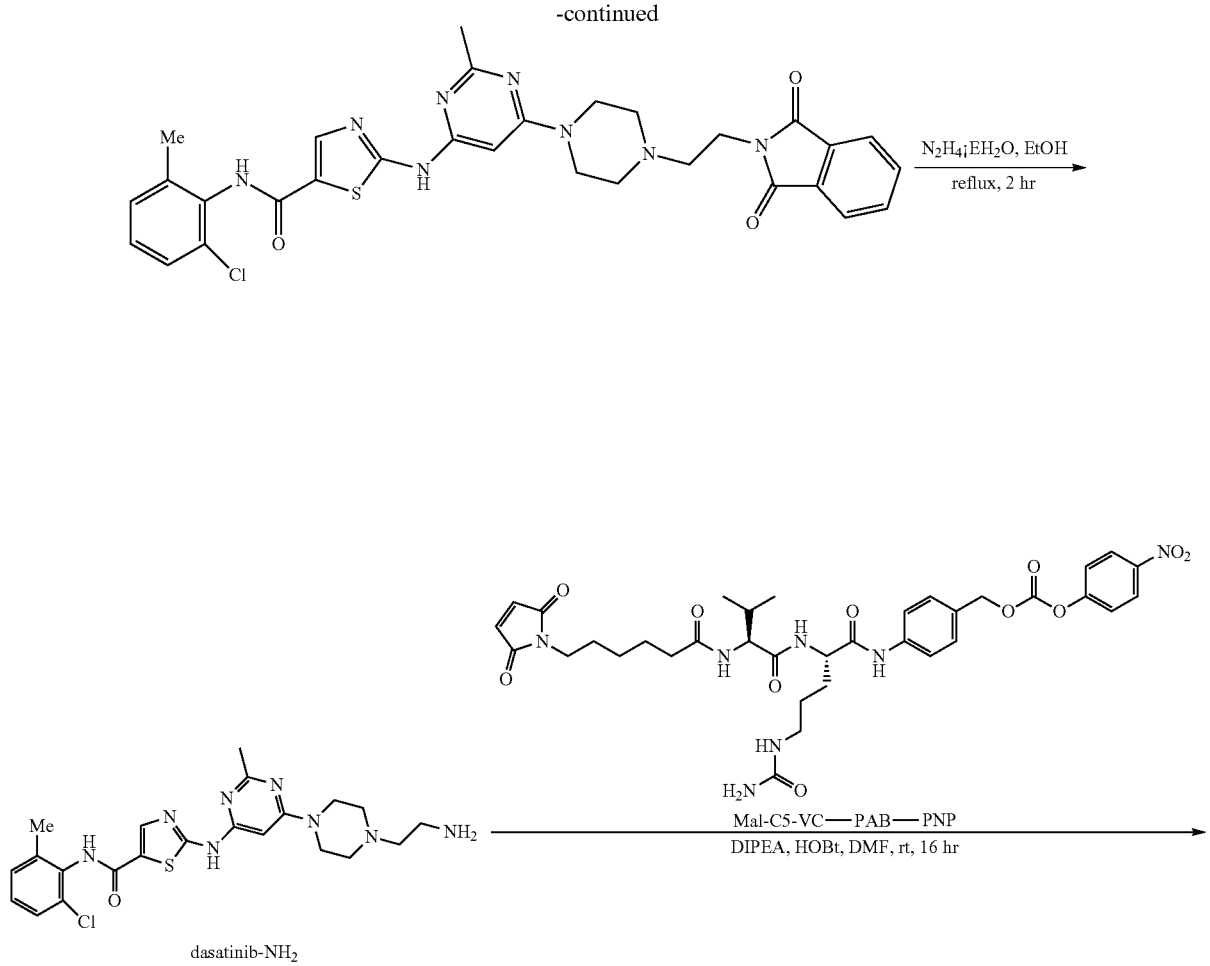
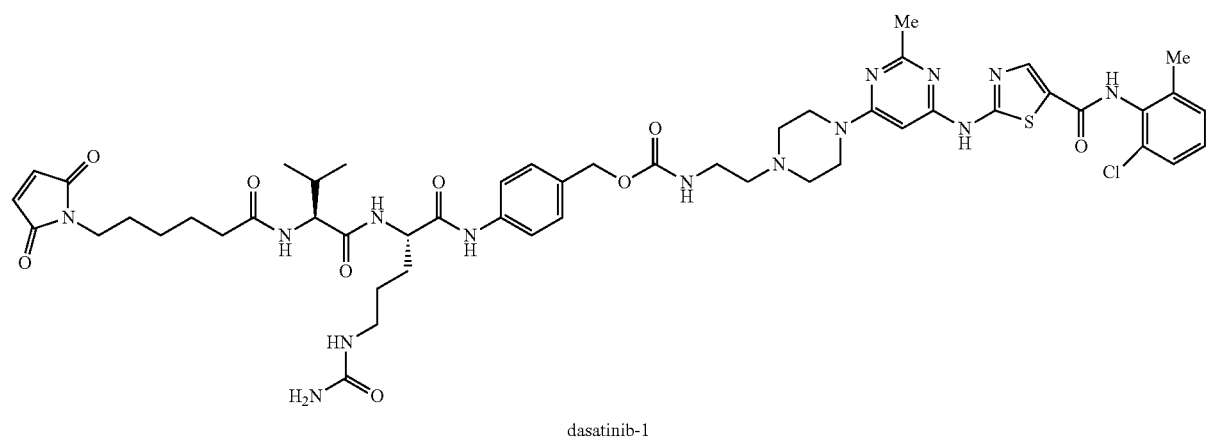

Referring to scheme 3, to a solution of dasatinib-NH₂ (31.9 mg, 0.0655 mmol), Mal-C5-VC-PAB-PNP (57.9 mg, 0.0786 mmol) and HOBt (10 mg, 0.0655 mmol) in DMF (0.5 ml), and N,N-diisopropylethylamine (DIPEA) (22.8 uL, 0.131 mmol) were added under argon. The reaction mixture was stirred at room temperature for 16 hours and then quenched with water. The solution was extracted with ethyl acetate. The organic layer was washed with brine, dried over MgSO₄(s), and concentrated under reduced pressure to give dasatinib-1 (12.5 mg) as a pale white solid in 17.6% yield. LC/MS m/z 1085.6.

Scheme 4 below shows the synthetic scheme of dasatinib-2 with a non-cleavable linker. The amine group of dasatinib-NH₂ was converted to isothiocyanate group by CS₂ and N,N'-Dicyclohexylcarbodiimide (DCC). The product dasatinib-1 can then be conjugate with an antibody through thioether bond formation.

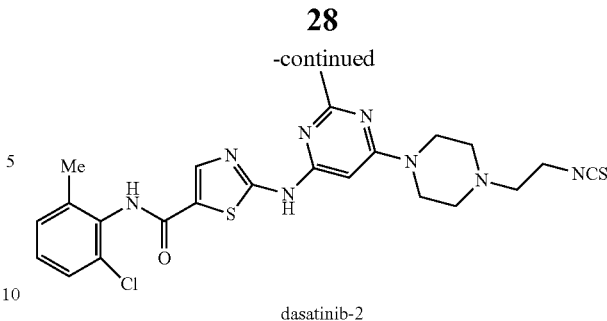

dasatinib-2

Referring to scheme 4, N,N'-Dicyclohexylcarbodiimide (50.3 mg, 0.244 mmol) in CH₂Cl₂ (3 ml) and CS₂ (244.3 uL, 4.06 mmol) were added to a solution of dasatinib-NH₂ (100 mg, 0.203 mmol) under argon. The mixture was stirred for 5 min at low temperature. The ice bath was removed, and then the mixture was stirred at room temperature until the reaction was complete. The reaction was concentrated under reduced pressure to remove the solvent, and then purified by silica gel column chromatography to obtain dasatinib-2 (16.9 mg) as a white solid. ¹H NMR (400 MHz, DMSO-d₆): δ ppm 11.47 (s, 1H), 9.88 (s, 1H), 8.23 (s, 1H), 7.40 (dd, J=1.2, 7.2 Hz, 1H), 7.24-7.30 (m, 2H), 6.07 (s, 1H), 3.80 (t, J=6.0 Hz, 2H), 3.54 (br, 4H), 2.66 (t, J=6.0 Hz, 2H), 2.54 (br, 4H), 2.42 (s, 3H), 2.24 (s, 3H). ESI-MS m/z 529.6.

Scheme 5 below shows the synthetic scheme of dasatinib-3 the derivatives with non-cleavable NHS linker. The amine group of dasatinib-NH₂ could be converted to carboxylic acid group by reductive amination with 4-formylbenzoic acid. The acid group could be converted to NHS group by N-Hydroxysuccinimide (HOSu) and 1-Ethyl-3-(3-dimethylaminopropyl)carbodiimide (EDCI) treatment. The product dasatinib-3 could conjugate with the lysine of the antibody through amide bond formation.

Scheme 4

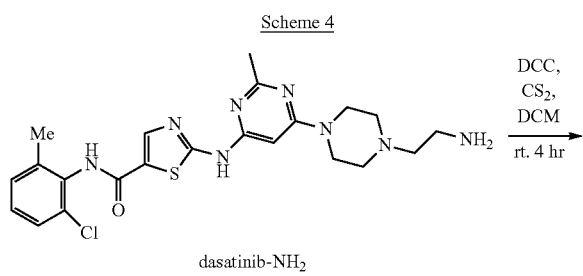

dasatinib-NH₂

Scheme 5

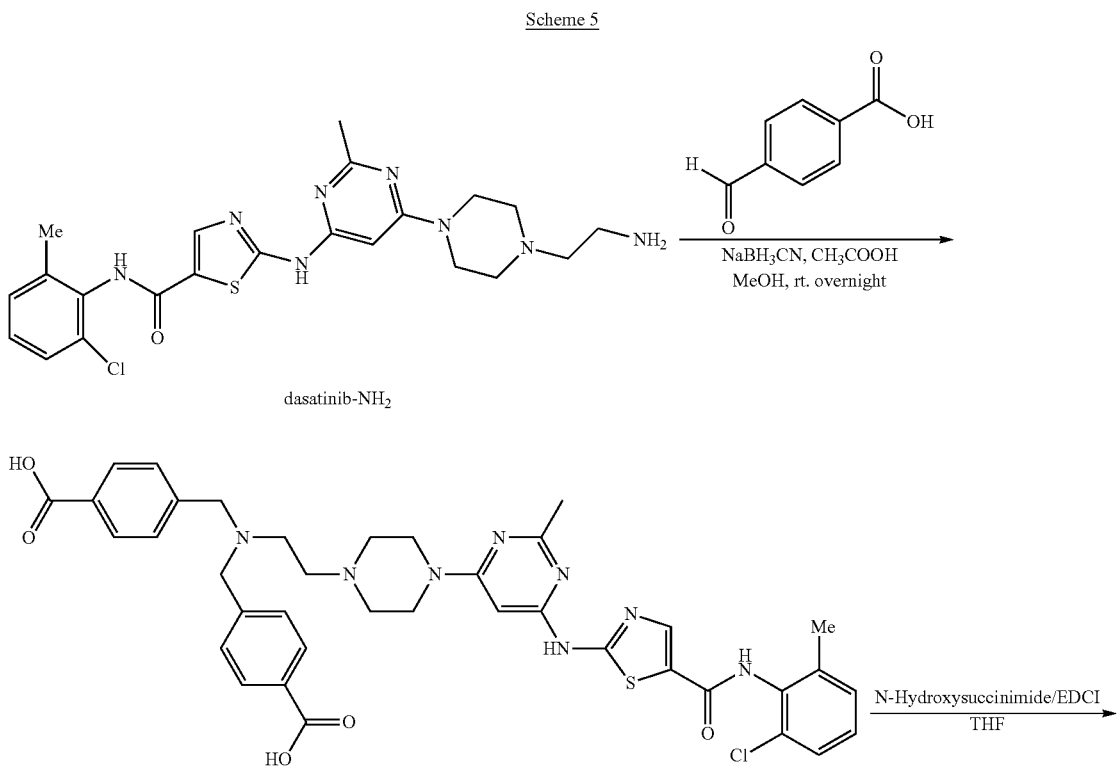

-continued

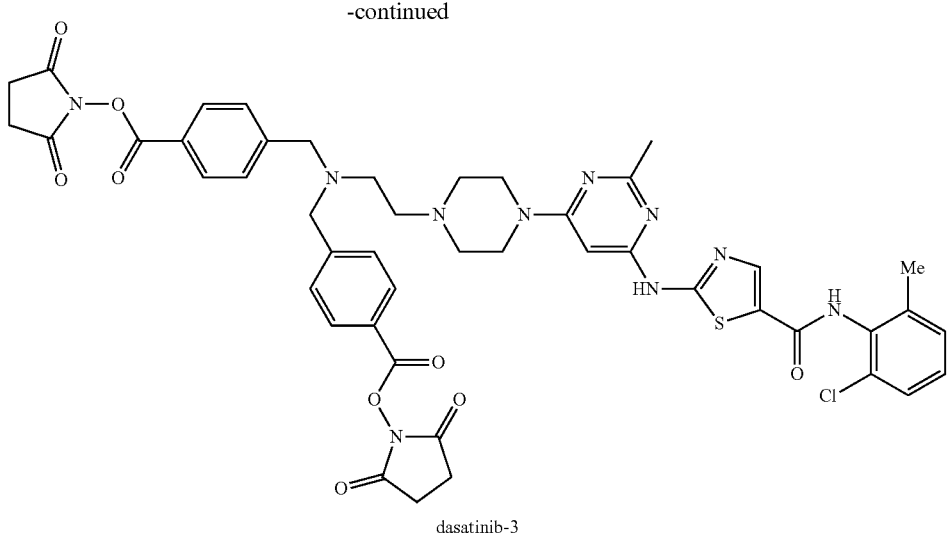

dasatinib-3

Referring to scheme 5, to a solution of 4-formylbenzoic acid (46.2 mg, 0.308 mmol) in 2 mL MeOH, dasatinib-NH$_2$ (100 mg, 0.205 mmol) in 1.5 mL MeOH, NaBH$_3$CN (28.3 mg, 0.451 mmol), and acetic acid (117 uL, 2.05 mmol) were added. The mixture was stirred at room temperature overnight. The solvent was then removed under reduced pressure. The residue was used in the next reaction without further purification.

Compound 2 dissolved in 1 mL DMF was added NHS (9.4 mg, 0.0815 mmol), EDCI (26.1 mg, 0.136 mmol) and DMAP (1.7 mg, 0.0136 mmol) then stirred at room temperature for overnight. The solution was extracted with ethyl acetate, the organic layer was washed with brine, dried over MgSO$_4$(s), and concentrated under reduced pressure. The crude was purified by column chromatography, to give dasatinib-3 as light yellow solids. 0.1H NMR (400 MHz, DMSO-d6): δ ppm 11.45 (s, 1H), 9.88 (s, 1H), 8.21 (s, 1H), 8.09-8.07 (d, J=8.2 Hz, 4H), 7.70-7.68 (d, J=8.2 Hz, 4H), 7.40-7.39 (d, J=7.5 Hz, 1H), 7.29-7.24 (m, 2H), 6.03 (s, 1H), 3.78 (s, 4H), 3.48 (s, 4H), 2.89 (s, 8H), 2.61-2.52 (m, 4H), 2.40-2.39 (m, 7H), 2.23 (s, 3H). ESI-MS m/z 949.4.

Example 4: Conjugation, Purification, and Structural Analysis of Antibody-Drug Conjugates Staurosporine 1, staurosporine 2, dasatinib-1, dasatinib-2, and dasatinib-3 were each conjugated to cetuximab as shown in FIG. 2. Conjugates Rex-1, Rex-2, Rex-3, Rex-4, and Rex-5 were generated.

Rex-1, Rex-2, Rex-3, and Rex-5 were prepared by conjugating the linker-payload to lysine residues in cetuximab. Generally, to a 333 μL solution of cetuximab (3.0 mg/mL) in buffer (50 mM potassium phosphate, 50 mM sodium chloride, 2 mM EDTA; pH 6.5), 20 equivalent of linker-kinase inhibitor (5 mM in DMSO) was slowly added. The reaction mixture was stirred under argon under 37° C. for 4 hours. The antibody preparation was desalted and concentrated using the Amicon Ultra-15 centrifugal filter device with 30 kDa NMWL in pH 7.4 PBS buffer to yield the antibody-drug conjugate. HRMS was used to determine the average drug-to-antibody ratio (DAR). The conjugation conditions are shown in Table 1 below.

TABLE 1

Conjugation conditions

| Conjugate | Linker-Payload (eq) | pH | % of Glycerol | Temperature (° C.) | Time (hr) | DAR |
|---|---|---|---|---|---|---|
| Rex-1-01 | 10 | 7.4 | | 20 | 4 | 1.09 |
| Rex-1-02 | 10 | 6.5 | | 37 | 4 | 4.96 |
| Rex-1-03* | 20 | 6.5 | | 37 | 4 | 2.67 |
| Rex-1-04* | 20 | 6.5 | | 37 | 4 | 3.11 |
| Rex-1-05 | 10 | 7.4 | | 37 | 4 | ≈1 |
| Rex-1-06 | 20 | 7.4 | | 37 | 4 | 2.76 |
| Rex-1-07 | 10 | 8.0 | | 37 | 4 | 3.43 |
| Rex-1-08* | 10 | 8.0 | | 37 | 4 | 1.98 |
| Rex-1-09 | 10 | 8.0 | | 37 | 2 | 3.11 |
| Rex-1-10 | 5 | 8.0 | | 37 | 4 | 2.18 |
| Rex-1-11 | 20 | 8.0 | | 37 | 4 | 1.77 |
| Rex-1-12* | 10 | 8.0 | 10% | 37 | 4 | 5.40 |
| Rex-1-13* | 10 | 8.0 | 20% | 37 | 4 | 5.48 |
| Rex-1-14* | 10 | 8.0 | 30% | 37 | 4 | 4.30 |
| Rex-1-15 | 10 | 6.5 | 10% | 37 | 4 | 1.12 |
| Rex-1-16 | 10 | 6.5 | 30% | 37 | 4 | 1.96 |
| Rex-1-17 | 10 | 6.5 | 20% | 37 | 16 | 1.04 |
| Rex-1-18 | 10 | 8.0 | 20% | 37 | 16 | 3.68 |
| Rex-2-01 | 10 | 6.5 | | 25 | 20 | <1 |
| Rex-4-01 | 10 | 8.0 | 20% | 37 | 16 | <1 |
| Rex-4-02 | 10 | 8.0 | 20% | 37 | 4 | <1 |
| Rex-4-03 | 10** | 8.0 | 20% | 37 | 4 | <1 |
| Rex-4-04 | 10 | 6.5 | 20% | 37 | 4 | <1 |
| Rex-4-05 | 10 | 7.4 | 20% | 37 | 4 | <1 |
| Rex-5-01 | 7.7 | 8.0 | 10% | 37 | 16 | <1 |

*Proper DAR and sufficient quantity for drug efficacy measurement.
**Linker-Payload dissolved in dimethylacetamide.

To prepare Rex-3, the linker-payload was conjugated to cetuximab via its cysteine residues. 1 mg of cetuximab (5 mM) was treated with 5.5 μL of 10 mM TCEP (8 molar equivalent) in 25 mM Na-borate, 25 mM NaCl, 1 mM DTPA, pH 8 buffer (with 20% glycerol) for 2 h at 37° C. The excess TCEP was purified away using Amicon (Millipore) Ultra-15 30K centrifugal filter. Partially reduced Cetuximab was then cooled to 0-4° C. and alkylated with 10 molar equivalents of dasatinib-1 for 30 min. 33.4 μL of 2 mM cysteine was used to quench the unreacted, excess dasatinib-1. Desalt and concentrate the antibody preparation using the Amicon Ultra-15 centrifugal filter device with 30 kDa NMWL in pH 7.4 PBS buffer to give Rex-3. HRMS were used to determine the average DAR. The conjugation conditions are shown in Table 2 below.

TABLE 2

| Conjugate | Equivalent of TCEP/dasatinib-1 | pH | % of Glycerol | Temperature (° C.) reduction/conjugation | Time (hr) | DAR |
|---|---|---|---|---|---|---|
| Rex-3-01 | 8/10 | 8.0 | | 37/4 | 2/0.5 | <1 |
| Rex-3-02* | 8/10 | 8.0 | 20% | 37/4 | 2/0.5 | 3.08 |
| Rex-3-03 | 8/6.3 | 7.4 | 20% | 37/4 | 2/0.5 | 1.67 |
| Rex-3-04 | 8/10 | 8.0 | 20% | 37/37 | 2/0.5 | 2.40 |
| Rex-3-05 | 15/10 | 8.0 | 20% | 37/4 | 2/0.5 | 1.14 |

*Proper DAR and sufficient quantity for drug efficacy measurement.

Some of the conjugates (i.e., Rex-1-04, -1-05, -1-06, -1-07, -1-09, -1-10, -1-15, -1-16, -1-17, -1-18, -4-01, -4-02, -4-03, -4-04, and -4-05) were analyzed using SDS-PAGE, e.g., 4-12% non-reducing and reducing SDS-PAGE gels, to confirm whether they retained the property antibody structure. All of the conjugates were analyzed by LC-MS as described below.

To carry out intact mass measurement, the conjugated antibody was reacted with PNGase F (enzyme:protein ratio of 1:100) at 37° C. for 3 h to remove N-glycans before analysis. The resulting solution was dried and re-dissolved in 0.2% (v/v) formic acid with a final concentration of 0.1 µg/µL. 9.8 µL of the solution was injected onto Waters ACQUITY UPLC system equipped with MassPREP micro desalting column (20 um, 2.1×5 mm Waters Corporation, Milford, Mass., USA) which was online-coupled to a Xevo™ G2S QTof instrument (Waters Corporation, Milford, Mass., USA). Mobile phase A was 0.1% FA in water, while mobile phase B was 0.1% FA in CAN. The elution gradient consisted of an isocratic elution at 10% B for 0.5 min, followed by a linear gradient from 10% to 90% B over 2.9 min, and then to 10% B over 1 min, and finally an isocratic elution at 10% B for 1 min. The flow rate was maintained at 0.2 mL/min throughout the elution. The column temperature was maintained at 60° C. The desolvation gas and source temperature of mass spectrometric analysis were set to 450° C. and 150° C., respectively. The capillary and cone voltages were set at 3 kV and 40 V, respectively. The m/z scan range was set to 1500-3800. The data were collected by MassLynx 4.1 software. The acquired multiple charge profiles were deconvoluted by using MaxEnt 1 algorithm. For deconvolution, the m/z range from 2,000-3,500 (Intact protein) was used with the mass range from 140,000 to 160,000 Da; minimum intensity ratio left and right, 40%; simulated isotope pattern spectrometer blur width of 1.6 Da; and number of iterations, 20.

For LC-MS analysis, a volume of 1 µL of the resulting solution was injected onto Waters nanoACQUITY UPLC system equipped with a precolumn (Waters, 0.180 mm×20 mm, 5 µm C18) followed by a nanocolumn (Waters, 75 µm×25 cm, 1.7 µm C18) in series coupled online to an LTQ-Orbitrap XL mass spectrometer (Thermo Fisher Scientific, San Jose, Calif., U.S.A.). Mobile phase A was 0.1% FA in water, whereas mobile phase B was 0.1% FA in CAN. The elution program consisted of an isocratic elution at 5% B for 5 min, a linear gradient from 5% to 40% B over 35 min followed by another linear gradient from 40% to 90% B over 5 min, and finally an isocratic elution at 90% B for 5 min. The flow rate was maintained at 0.3 µL/min. The LTQ-Orbitrap XL mass spectrometer was operated as the following: survey full-scan MS spectra (m/z 300-2000) were acquired in the Orbitrap with a mass resolution of 60 000 at m/z 400 (with an ion target value of $5×10^5$ ions). The five most intense peaks with charge state ≥2 were selected for sequencing and fragmented in the ion trap with normalized collision energy of 35%, activation q=0.25, activation time of 30 ms, and one microscan. The target value was $1×10^4$. The ion selection threshold was 5000 counts, and the maximum allowed ion accumulation times were 500 ms for full scans and 30 ms for CID.

Example 5: Efficacy of Conjugate Rex-1

SW48 colon cancer cells (carrying wild-type BRAF and KRAS), HT-29 colon cancer cells (carrying a BRAF mutation), and SW480 colon cancer cells (carrying a KRAS mutation) were individually treated with cetuximab, staurosporine, cetuximab and staurosporine combined, and Rex-1. As shown in FIG. 3, SW48 cells, but not HT-29 cells or SW480 cells, were sensitive to cetuximab. Rex-1 reduced the viability of SW48 cells by two folds as compared to cetuximab. Notably, Rex-1 showed efficacy against HT-29 cells and SW480 cells, resulting in about 50% viability in both cells. Also, Rex-1 was significantly more effective than the combination of cetuximab and staurosporine in all three cell lines.

Different lots of Rex-1 (shown in Table 1 above) were analyzed. While they demonstrated varied efficacy against HT-29 cells or SW480 cells, they were all significantly more effective than the combination of cetuximab and staurosporine with respect to SW48 cells. See FIG. 4 and Table 3.

TABLE 3

Efficacy of different lots of Rex-1

| Cells | Rex-1-03 | Rex-1-04 | Rex-1-08 | Rex-1-12 | Rex-1-13 | Rex-1-14 |
|---|---|---|---|---|---|---|
| SW48 | +++++ | +++++ | +++++ | ++++ | ++++ | ++++ |
| HT-29 | +++ | +++++ | ++ | ++++ | +++ | N.A. |
| SW480 | ++ | +++++ | ++ | ++++ | +++ | ++ |

N.A.: not available

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. An immunoconjugate, comprising an anti-EGFR antibody or a binding fragment thereof, and a kinase inhibitor, wherein the immunoconjugate has the following formula:

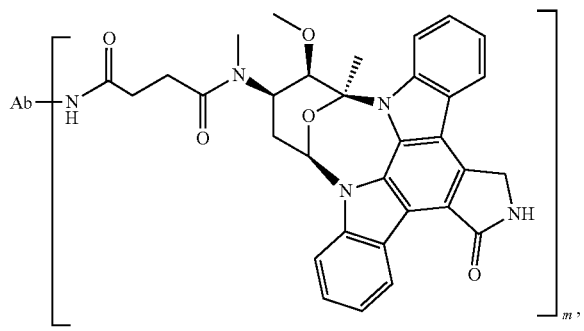

in which Ab is cetuximab; and m is an integer of 1-20.

2. The immunoconjugate of claim 1, wherein m is 2 to 8.

3. A pharmaceutical composition, comprising the immunoconjugate of claim 1 and a pharmaceutically acceptable carrier.

4. The pharmaceutical composition of claim 3, further comprising another therapeutic agent.

5. A method of treating a cancer in a subject, comprising administering an effective amount of the immunoconjugate of claim 1 to the subject.

6. The method of claim 5, wherein the cancer in the subject is resistant to an anti-EGFR antibody or a binding fragment thereof, or an EGFR tyrosine kinase inhibitor.

7. The method of claim 6, wherein the cancer has a mutation in KRAS, BRAF, PIK3CA, PTEN, EGFR, P53, or SRC.

8. The method of claim 7, further comprising, prior to the administering step, determining whether the cancer has the mutation.

9. The method of claim 5, wherein the cancer is a colorectal cancer, head and neck cancer, gastrointestinal cancer, lung cancer, breast cancer, pancreatic cancer, ovarian cancer, cervical cancer, prostate cancer, kidney cancer, brain cancer, renal carcinoma, glioma, bladder cancer, oral cancer, or EGFR-positive cancer.

10. The method of claim 9, further comprising administering another therapeutic agent to the subject.

* * * * *